(12) United States Patent
Tahmasebi Maraghoosh et al.

(10) Patent No.: US 10,646,279 B2
(45) Date of Patent: May 12, 2020

(54) IMAGING APPARATUS FOR BRACHYTHERAPY OR BIOPSY

(71) Applicant: KONINKLIJKE PHILIPS N.V., Eindhoven (NL)

(72) Inventors: Amir Mohammad Tahmasebi Maraghoosh, Ridgefield, CT (US); Shyam Bharat, Cortlandt Manor, NY (US); Ehsan Dehghan Marvast, New York, NY (US); Vijay Parthasarathy, Mt. Kisco, NY (US)

(73) Assignee: Koninklijke Philips N.V., Eindhoven (NL)

( * ) Notice: Subject to any disclaimer, the term of this patent is extended or adjusted under 35 U.S.C. 154(b) by 1070 days.

(21) Appl. No.: 14/782,333

(22) PCT Filed: Apr. 4, 2014

(86) PCT No.: PCT/IB2014/060419
§ 371 (c)(1),
(2) Date: Oct. 5, 2015

(87) PCT Pub. No.: WO2014/167467
PCT Pub. Date: Oct. 16, 2014

(65) Prior Publication Data
US 2016/0030130 A1 Feb. 4, 2016

Related U.S. Application Data

(60) Provisional application No. 61/811,167, filed on Apr. 12, 2013.

(51) Int. Cl.
*A61B 34/20* (2016.01)
*A61B 10/02* (2006.01)
(Continued)

(52) U.S. Cl.
CPC ............ *A61B 34/20* (2016.02); *A61B 8/0841* (2013.01); *A61B 8/12* (2013.01); *A61B 8/4209* (2013.01);
(Continued)

(58) Field of Classification Search
CPC ..... A61B 34/20; A61B 8/4245; A61B 8/0841; A61B 8/12; A61B 8/4209; A61B 8/483;
(Continued)

(56) References Cited

U.S. PATENT DOCUMENTS 6,142,991 A 11/2000 Schatzberger
6,529,765 B1 * 3/2003 Franck .................. A61B 90/10
600/427
(Continued)

FOREIGN PATENT DOCUMENTS

JP H06205776 A 7/1994
JP H08229042 A 9/1996
(Continued)

OTHER PUBLICATIONS

Mung, J. et al. "A non-disruptive technology for Robust 3D Tool Tracking for Ultrasound-Guided Interventions", Sep. 18, 2011, Medical Image Computing and Computer-Assisted Intervention a Miccai 2011., pp. 153-160.
(Continued)

*Primary Examiner* — Peter Luong

(57) ABSTRACT

The invention relates to an imaging apparatus (24) for imaging an introduction element (17) like a needle or a catheter for performing a brachytherapy or a biopsy. A tracking unit (3, 4) tracks the location of the introduction element within a living being (2), an imaging unit (6) like an ultrasound imaging unit generates an image showing an inner part of the living being, which includes the tracked location of the introduction element, based on the tracked (Continued)

location, and a display (7) displays the image. During the brachytherapy or biopsy the display can always show the introduction element, without requiring a manual control. For instance, it is not necessary that a physician manually controls the position and image plane of the imaging unit. This allows for an accurate and fast insertion of the introduction element into the living being such that a target region is reliably reached.

17 Claims, 7 Drawing Sheets

(51) Int. Cl.
| | |
|---|---|
| *A61B 8/12* | (2006.01) |
| *A61B 8/08* | (2006.01) |
| *A61B 8/00* | (2006.01) |
| *A61N 5/10* | (2006.01) |
| A61B 17/34 | (2006.01) |
| A61B 90/00 | (2016.01) |
| A61B 10/04 | (2006.01) |

(52) U.S. Cl.
CPC ........ *A61B 8/4245* (2013.01); *A61B 10/0241* (2013.01); *A61N 5/1027* (2013.01); *A61N 5/1049* (2013.01); *A61B 8/465* (2013.01); *A61B 8/469* (2013.01); *A61B 8/483* (2013.01); *A61B 8/523* (2013.01); *A61B 2010/045* (2013.01); *A61B 2017/3411* (2013.01); *A61B 2034/2051* (2016.02); *A61B 2034/2059* (2016.02); *A61B 2034/2061* (2016.02); *A61B 2034/2063* (2016.02); *A61B 2034/2065* (2016.02); *A61B 2090/378* (2016.02); *A61B 2576/00* (2013.01); *A61N 2005/1012* (2013.01); *A61N 2005/1051* (2013.01); *A61N 2005/1058* (2013.01)

(58) Field of Classification Search
CPC ......... A61B 8/469; A61B 8/465; A61B 8/523; A61B 10/0241; A61B 2034/2065; A61B 2034/2051; A61B 2034/2059; A61B 2034/2061; A61B 2034/2063; A61B 2090/378; A61B 2010/045; A61B 2576/00; A61B 2017/3411; A61N 5/1027; A61N 5/1049; A61N 2005/1012; A61N 2005/1051; A61N 2005/1058

See application file for complete search history.

(56) References Cited

U.S. PATENT DOCUMENTS

| | | | |
|---|---|---|---|
| 6,665,554 | B1 * | 12/2003 | Charles .................. A61B 90/36 600/427 |
| 7,527,593 | B2 | 5/2009 | Fidel et al. |
| 8,118,818 | B2 | 2/2012 | Zheng et al. |
| 8,788,019 | B2 | 7/2014 | Downey et al. |
| 9,256,947 | B2 | 2/2016 | Gauthier et al. |
| 2002/0143229 | A1 | 10/2002 | Green et al. |
| 2003/0135115 | A1 | 7/2003 | Burdette et al. |
| 2005/0107688 | A1 | 5/2005 | Strommer |
| 2006/0079745 | A1 | 4/2006 | Viswanathan |
| 2007/0049822 | A1 | 3/2007 | Bunce et al. |
| 2007/0167769 | A1 | 7/2007 | Ikuma et al. |
| 2010/0019918 | A1 | 1/2010 | Avital et al. |
| 2011/0261180 | A1 | 10/2011 | Simon et al. |
| 2011/0301593 | A1 | 12/2011 | Teichman et al. |
| 2012/0203095 | A1 | 8/2012 | Krieger et al. |
| 2013/0102891 | A1 | 4/2013 | Binnekamp et al. |
| 2013/0195313 | A1 | 8/2013 | Gauthier et al. |
| 2014/0187919 | A1 | 7/2014 | Parthasarathy et al. |

FOREIGN PATENT DOCUMENTS

| | | |
|---|---|---|
| JP | H09229042 A | 9/1997 |
| JP | 2006346477 A | 12/2006 |

OTHER PUBLICATIONS

Hakime, A. et al., "Electromagnetic-Tracked Biopsy under Ultrasound Guidance: Preliminary Results", Cardiovascular and Interventional Radiology, vol. 35, No. 4, Sep. 27, 2011, pp. 898-905.

Chen, T.K. et al. "Automated intraoperative calibration for prostate cancer brachytherapy", Med. Phys. 38(11), Nov. 2011, pp. 6285-6299.

* cited by examiner

IMAGING APPARATUS FOR BRACHYTHERAPY OR BIOPSY

CROSS-REFERENCE TO PRIOR APPLICATIONS

This application is the U.S. National Phase application under 35 U.S.C. § 371 of International Application Serial No, PCT/IB2014/060419, filed on Apr. 4, 2014, which claims the benefit of U.S. Application Ser. No. 61/811,167, filed on Apr. 12, 2013. These applications are hereby incorporated by reference herein.

FIELD OF THE INVENTION

The invention relates to an imaging apparatus, an imaging method and an imaging computer program for imaging an introduction element like a catheter or a needle within a living being during a brachytherapy or a biopsy. The invention relates further to a system for performing a brachytherapy or a biopsy comprising the imaging apparatus.

BACKGROUND OF THE INVENTION

In low-dose rate (LDR) brachytherapy and high-dose rate (HDR) brachytherapy an introduction element like a catheter or a needle for introducing a radiation source is inserted into a person by a physician under ultrasound imaging guidance, in order to treat an inner region of the person with radiation emitted by the radiation source. During the insertion process the physician has to manually control the position and image plane of an ultrasound transducer, which leads to inaccuracies in imaging such that the tip of the introduction element is not always visualized accurately relative to a target region within the person, where the tip should be finally located. The physician performs therefore often an iterative process comprising multiple attempts to guide the tip of the introduction element to the target region. This leads to a temporally long and not very accurate insertion process.

SUMMARY OF THE INVENTION

It is an object of the present invention to provide an imaging apparatus, an imaging method and an imaging computer program for imaging an introduction element within a living being during a brachytherapy or a biopsy, which allows inserting the introduction element faster and more accurately.

In a first aspect of the present invention an imaging apparatus for imaging an introduction element within a living being is presented, the introduction element being adapted to be inserted into the living being for performing a biopsy or for introducing a radiation source into the living being for performing a brachytherapy, wherein the imaging apparatus comprises:
- a tracking unit for tracking the location of the introduction element within the living being,
- an imaging unit for generating an image showing an inner part of the living being, which includes the tracked location of the introduction element, based on the tracked location, and
- a display for displaying the image.

Since the location of the introduction element within the living being, which is a person or an animal, is tracked by the tracking unit and since the imaging unit generates an image showing an inner part of the living being, which includes the tracked location of the introduction element, based on the tracked location, wherein the generated image is finally shown on a display, during the insertion process the display can always display an image showing the current location of the introduction element within the living being, without requiring a user to manually control the imaging unit. For instance, it is not necessary that a physician manually controls the position and image plane of the imaging unit to image a tip of the introduction element during the insertion procedure. This allows for a more accurate and faster insertion of the introduction element into the living being such that a target region is reliably reached.

The introduction element is preferentially a needle or a catheter to be inserted under image guidance, wherein the introduction element is preferentially adapted to perform a biopsy and/or to introduce a radioactive radiation source into the living being. In particular, the imaging apparatus is adapted to image the introduction element during an insertion process for performing a biopsy, an LDR brachytherapy or a HDR brachytherapy. It is further preferred that the imaging apparatus is adapted to image the introduction element during a prostate biopsy, an LDR prostate brachytherapy or a HDR prostate brachytherapy.

The imaging unit is preferentially adapted to update the generated image in realtime based on the tracked location of the introduction element, wherein the display is adapted to display the updated image in realtime. It is preferentially an ultrasound imaging unit, in particular, a transrectal ultrasound imaging unit. For instance, the imaging unit may comprise a three-dimensional ultrasound probe, i.e. a two-dimensional array of ultrasound transducers, for covering a three-dimensional region within the living being. However, the imaging unit may also comprise a two-dimensional ultrasound probe, i.e. a one-dimensional array of ultrasound transducers, covering a two-dimensional region within the living being. Using ultrasound for imaging inner parts of the living being allows generating high-quality images without damaging tissue of the living being.

It is preferred that the introduction element is an elongated element having a tip and an elongated body to be inserted into the living being through an opening within a holding element for holding the introduction element, wherein in an embodiment the tracking unit comprises a linear encoder for determining a linear location of the tip of the introduction element relative to the opening, while being inserted into the living being through the opening of the holding element, wherein the tracking unit is adapted to determine the location of the tip and/or of the elongated body of the introduction element within the living being based on the determined linear location and a known location of the opening. For instance, the location of the tip can be determined by vectorially adding the determined linear location to the known location of the opening. The location of the elongated body within the living being may be determined as the length between the determined linear location of the tip and the known location of the opening. Using a linear encoder, which may be an absolute encoder and an incremental encoder, allows determining the location of the introduction element within the living being in a technically relatively simple way, which yields particularly accurate results, if it can be assumed that the introduction element travels substantially in a straight line within the living being.

The introduction element may comprise a scale on its outer surface, wherein the linear encoder may be adapted to read the scale on the outer surface of the introduction element and to determine the linear location of the introduction element based on the read scale. The linear encoder can be adapted to read an optically detectable scale, a magnetically detectable scale, a capacitively detectable scale, an inductively detectable scale et cetera of the introduction element. However, the linear encoder can also be adapted to determine the linear location of the introduction element in another way, for instance, by using a gear-based encoding.

The imaging apparatus may further comprise an attaching element for attaching the linear encoder to an opening of the holding element, through which the introduction element is inserted into the living being. The holding element may comprise several openings, wherein the attaching element may be adapted to be movable between the openings of the holding element. This allows determining the linear location of the introduction element with respect to an arbitrary opening of the holding element, through which the introduction element is actually inserted. The imaging apparatus can further comprise a locking mechanism for locking and holding the attaching element at an opening. The holding element is preferentially a grid template comprising a grid of openings.

In an embodiment the tracking unit is adapted to track the location of the introduction element by electromagnetic tracking and/or optical shape sensing tracking. Using an electromagnetic tracking technology and/or an optical shape sensing tracking technology allows tracking the location of the introduction element within the living being very accurately, even if the introduction element is not straight, but curved. These technologies can therefore lead to an improved accuracy of the determination of the location of the introduction element within the living being. In case of optical shape sensing the entire length of the introduction element may be equipped with a shape sensing fiber such that the location of the entire length including the tip of the introduction element can be determined at any time during the insertion procedure. In case of electromagnetic tracking the tracking unit may be adapted to electromagnetically track the location of the tip of the introduction element. Moreover, the tracking unit may be adapted to store the tracked locations of the tip of the introduction element, which are tracked during insertion, in order to determine the location of the elongated body of the introduction element within the living being.

In a preferred embodiment the tracking unit is adapted to track the location of the tip of the introduction element, wherein the imaging unit is adapted to determine a tip slice within the living being including the tracked location of the tip of the introduction element and to generate a tip image representing the tip slice, wherein the display is adapted to display the generated tip image. Moreover, the imaging unit may be adapted to detect the tip of the introduction element within the tip image representing the determined tip slice by image processing, to determine a further tip slice including the detected tip of the introduction element, wherein the thickness of this further tip slice is smaller than the thickness of the initial, first tip slice, and to generate a further tip image representing the further tip slice, wherein the display is adapted to display the generated further tip image. The imaging unit may be adapted to determine an axial tip slice and/or a sagittal tip slice and to generate an axial tip image and/or a sagittal tip image representing the axial tip slice and/or the sagittal tip slice, respectively, wherein the display may be adapted to display the generated axial tip image and/or the sagittal tip image. Moreover, the imaging unit may be adapted to determine the tip slice such that it is perpendicular to the elongated body of the introduction element.

Furthermore, the tracking unit may be adapted to determine the location of the elongated body within the living being, wherein the imaging unit may be adapted to determine a body slice within the living being including a length of the elongated body and to generate a body image representing the body slice, wherein the display is adapted to display the generated body image. In particular, the imaging unit may be adapted to determine the body slice such that the determined body slice includes a maximal portion of the length of the elongated body. In an embodiment the imaging unit is adapted to determine further body slices including further portions of the length of the elongated body and to generate further body images representing the determined further body slices within the living being, wherein the display is adapted to display the further body images. The imaging unit may be adapted to determine an axial body slice and/or a sagittal body slice and to generate an axial body image and/or a sagittal body image representing the axial body slice and/or the sagittal body slice, respectively, wherein the display may be adapted to display the generated axial body image and/or the sagittal body image.

In an embodiment the tracking unit is adapted to track the locations of at least two different parts of the introduction element within the living being, wherein the imaging unit is adapted to generate at least two images showing at least two inner parts of the living being, which include the locations of the at least two different parts of the introduction element, based on the tracked locations and wherein the display is adapted to display the at least two images. The different parts of the introduction element are, for instance, a tip and an elongated body of the introduction element such that the display can show, for instance, an axial tip image and a sagittal body image. However, the display may also display more than two images and/or other images showing different parts of the introduction element like different sagittal body images.

In an embodiment the imaging apparatus further comprises a target location providing unit for providing a target location, where the introduction element is to be located within the living being, wherein the imaging unit is adapted to determine a target slice within the living being, which includes the target location, and to generate a target image representing the target slice, wherein the display is adapted to display the target image.

The imaging unit can be adapted to generate several of the above mentioned images substantially simultaneously such that they can be shown simultaneously side-by-side on the display. For instance, images representing two perpendicular planes can be generated and displayed, wherein one image is a tip image being perpendicular to the length of the elongated body of the introduction element and the other image can be a body image showing at least a portion of the length of the introduction element, or one image can be an axial tip image and the other image can be an axial target image.

In a further aspect of the present invention a system for performing a brachytherapy or a biopsy is presented, wherein the system comprises:
　　an introduction element for being inserted into a living being for performing a biopsy or for introducing a radiation source into the living being for performing a brachytherapy,
　　an imaging apparatus for imaging the introduction element within the living being as defined in claim 1.

If the system is adapted to perform a brachytherapy, it can further comprise the radiation source for treating the living being.

In a further aspect of the present invention an imaging method for imaging an introduction element within a living being is presented, the introduction element being adapted to be inserted into the living being for performing a biopsy or for introducing a radiation source into the living being for performing a brachytherapy, wherein the imaging method comprises:

tracking the location of the introduction element within the living being by using a tracking unit,
generating an image showing an inner part of the living being, which includes the tracked location of the introduction element, based on the tracked location by using an imaging unit, and
displaying the image by using a display.

In a further aspect of the present invention an imaging computer program for imaging an introduction element within a living being is presented, the introduction element being adapted to be inserted into the living being for performing a biopsy or for introducing a radiation source into the living being for performing a brachytherapy, wherein the imaging computer program comprises program code means for causing an imaging apparatus as defined in claim 1 to carry out the steps of the imaging method as defined in claim 14, when the imaging computer program is run on a computer controlling the imaging apparatus.

It shall be understood that the imaging apparatus of claim 1, the brachytherapy system of claim 13, the imaging method of claim 14, and the imaging computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
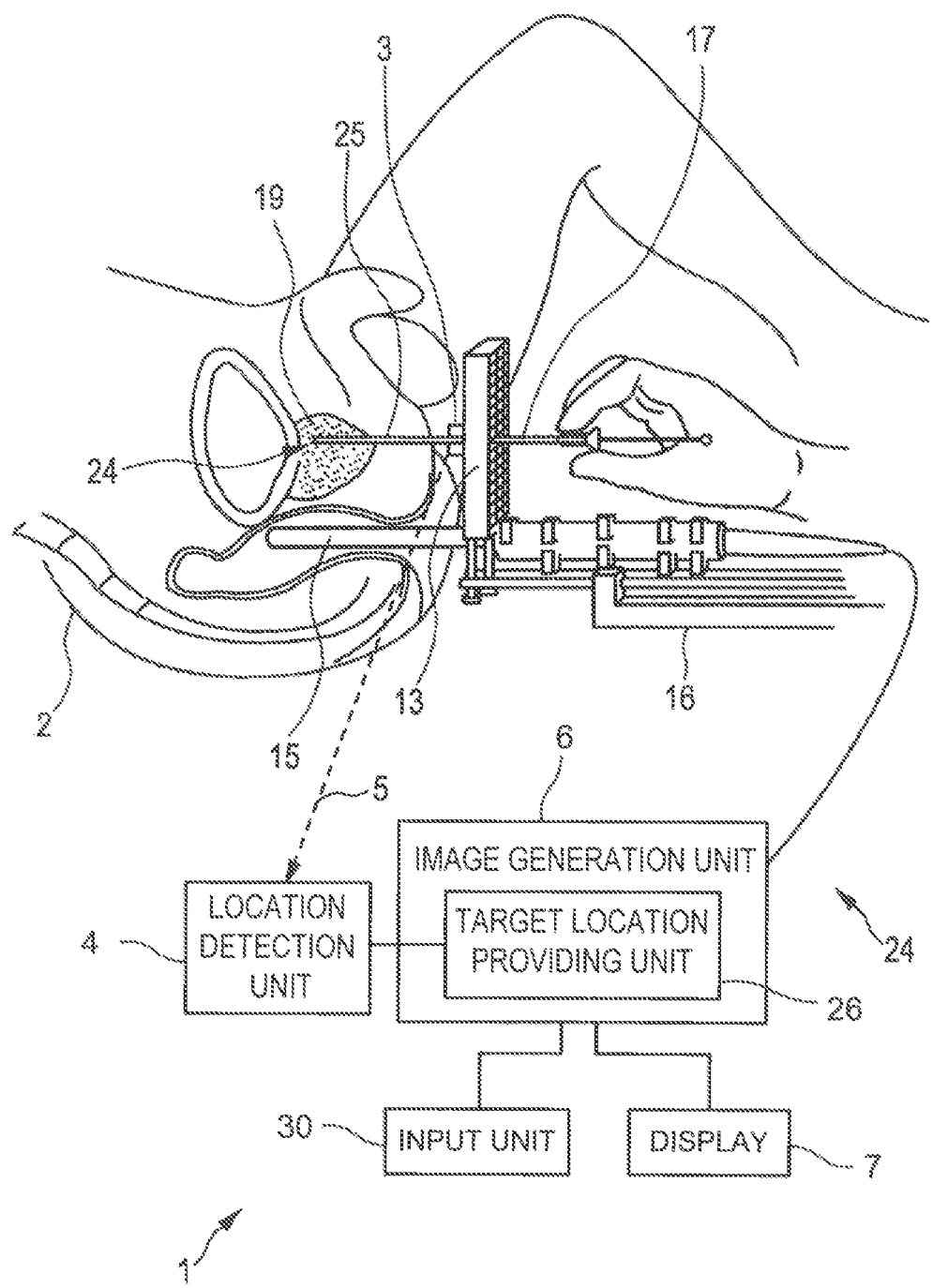
FIG. 1 shows schematically and exemplarily an embodiment of a brachytherapy system.

FIG. 1 shows schematically and exemplarily an embodiment of a brachytherapy system for performing a brachytherapy. The brachytherapy system 1 comprises an introduction element 17 for introducing a radiation source into a person 2. In this embodiment, the introduction element 17 is a needle, which is inserted into the prostate 19 of the person 2. During the insertion process an imaging apparatus 24 is used for imaging the introduction element 17 within the person 2.

The imaging apparatus 24 comprises a tracking unit 3, 4 for tracking the location of the introduction element 17 within the person 2, an imaging unit 6, 16 for generating an image showing an inner part of the person 2, which includes the tracked location of the introduction element 17, based on the tracked location, and a display 7 for displaying the image.

The introduction element 17 is manually inserted into the person 2, in particular, into the prostate 19, under image guidance. In particular, the imaging apparatus 24 is adapted to image the introduction element 17 during an insertion process for performing an LDR brachytherapy or a HDR brachytherapy, wherein the imaging unit 6, 15 is preferentially adapted to update the generated image in realtime based on the actual tracked location of the introduction element 17 within the person 2 and wherein the display 7 is adapted to display the updated image in realtime.

The introduction element 17 is an elongated element having a tip 24 and an elongated body 25 to be inserted into the person 2 through an opening 8 within a holding element 13 for holding the introduction element 17. The holding element 13 is a template grid with a two-dimensional grid of openings. It is schematically and exemplarily shown in more detail in FIG. 2.

Figure 2:
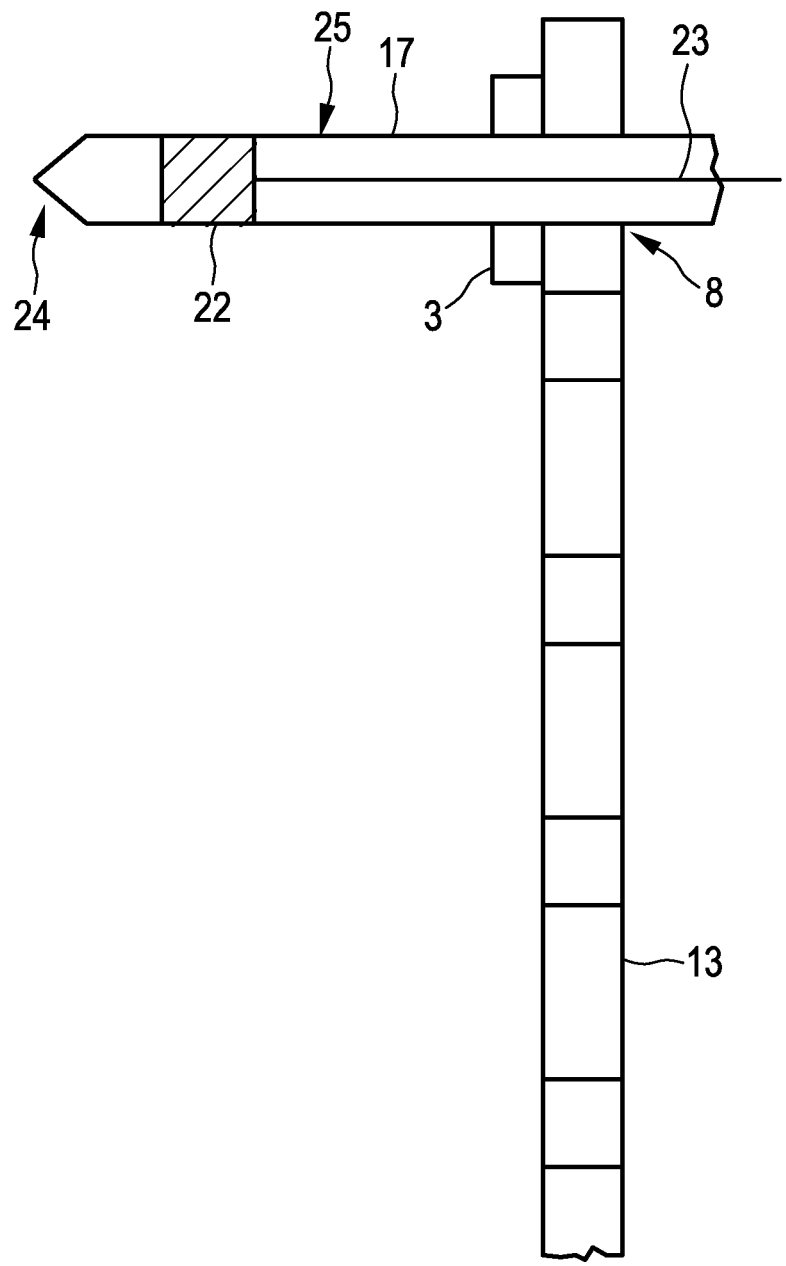
FIG. 2 shows schematically and exemplarily a sectional view of a grid template and an introduction element of the brachytherapy system, FIG. 3 schematically and exemplarily illustrates a bending of the introduction element, FIG. 4 schematically and exemplarily illustrates attaching elements for attaching a linear encoder on a surface of the grid template.

FIG. 2 is a sectional view showing the template grid 13 with the openings 8, wherein through one of these openings the introduction element 17 is inserted. Within the introduction element 17 the radiation source 22 for emitting radiation to a target region is located. The radiation source 22, which is preferentially a radioactive radiation source, can be moved within the introduction element 17 by using the connection 23, which may be a wire or another mechanical connection. At the opening 8, through which the introduction element 17 is inserted into the person 2, a linear encoder 3 of the tracking unit is attached. The linear encoder 3 is adapted to determine a linear location of the tip 24 of the introduction element 17 relative to the opening 8, while being inserted into the person 2 through the opening 8 of the grid template 13. The tracking unit further comprises a location determination unit 4 for determining the location of the tip 24 and/or of the elongated body 25 of the introduction element 17 within the person 2 based on the determined linear location and a known location of the opening 8, which can be measured before the insertion procedure. In particular, the location determination unit 4 can be adapted to vectorially add the determined linear location of the tip 24 of the introduction element 17 to the known location of the opening 8. The location of the elongated body 24 within the person 2 may be determined as the length between the determined linear location of the tip 24 and the known location of the opening 8. The linear encoder 3 can be an absolute encoder or an incremental encoder, which starts measuring the linear position of the tip 24 of the introduction element 17, when the tip 24 passes the linear encoder 3, while being inserted through the opening 8 into the person 2. The linear encoder 3 and the location determination unit 4 of the tracking unit can communicate with each other by using a wireless data connection 5. It may be a low-bandwidth data connection, a Bluetooth data connection or another wireless data connection.

The introduction element 17 may comprise a scale on its outer surface, wherein the linear encoder 3 may be adapted to read the scale on the outer surface of the introduction element 17 and to determine the linear location of the introduction element 17 based on the read scale. The linear encoder 3 can be adapted to read an optically detectable scale, a magnetically detectable scale, a capacitively detectable scale, an inductively detectable scale, et cetera of the introduction element 17, which may be formed by customly shaped stripes. However, the linear encoder 3 can also be adapted to determine the linear location of the tip 24 of the introduction element 17 in another way, which, for instance, does not require a scale on the introduction element. For example, the linear encoder 3 can be adapted to use a gear-based encoding, which does not need to comprise, for instance, coded stripes or bands forming a scale.

The imaging unit comprises a three-dimensional transrectal ultrasound probe 15 attached to a support element 16, to which also the template grid 13 is attached. The support element 16 ensures that the template grid 13 and the ultrasound probe 15 are fixed during the brachytherapy. Before the brachytherapy, in particular, before the insertion procedure, the imaging unit 6, 15 and the tracking unit 3, 4 have been registered with respect to each other such that a position in an image reference frame can be transformed to a position in a tracking reference frame and vice versa. Since the template grid 13 and the ultrasound probe 15 are fixed during the entire brachytherapy, this transformation for transforming locations between the image reference frame and the tracking reference frame is valid through the entire brachytherapy. Thus, for instance, the location of each opening 8 of the template grid 13 is known within the image reference frame, i.e. especially the location of the opening 8 of the grid template 13, through which the introduction element 17 is inserted into the person 2, is known in the image reference frame. Therefore, after the location of the tip 24 of the introduction element 17 has been determined based on the known location of the opening 8 of the grid template 13, through which the introduction element 17 is inserted, and the length of the portion of the introduction element 17, which has already been inserted into the person 2 through the opening 8, as determined by the linear encoder 3, the location of the tip 24 within the person 2 is also known in the reference imaging frame.

Figure 3:
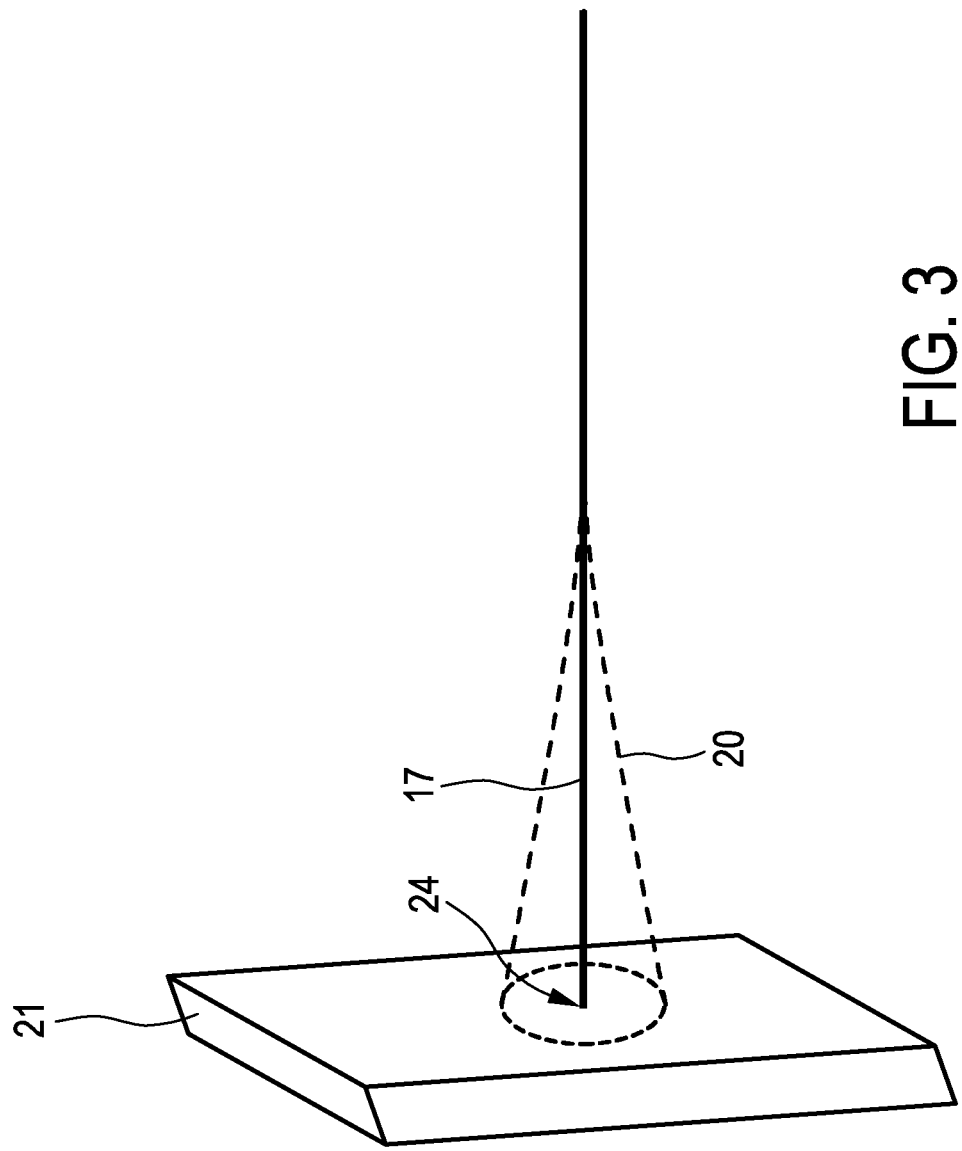

The imaging unit comprises the ultrasound probe 15 and an image generation unit 6. The tracking unit 3, 4 is adapted to track the location of the tip 24 of the introduction element 17 within the person 2, wherein the image generation unit 6 is adapted to determine a tip slice within the person 2 including the tracked location of the tip 24 of the introduction element 17 and to generate a tip image representing the tip slice. The display 7 is adapted to display the generated tip image. The image generation unit is preferentially further adapted to detect the tip 24 of the introduction element 17 within the tip image representing the determined tip slice by image processing, to determine a further tip slice including the detected tip 24 of the introduction element 17, wherein the thickness of the tip slice is larger than the thickness of the further tip slice, and to generate a further tip image representing the further tip slice, wherein the display 7 is adapted to display the generated further tip image. Thus, firstly a relatively broad initial tip slice may be determined, which takes into account that the introduction element 17 may be curved within the person 2 such that the linear position determined by the linear encoder 3 may not lead exactly to the real location of the tip 24 within the person 2. The width of this initial tip slice is preferentially chosen such that, considering the flexibility of the introduction element 17 and, thus, possible degrees of bending within the person 2, the real location of the tip 24 of the introduction 17 is surely within the initial tip slice. A thinner tip slice, which includes the real location of the tip 24 of the introduction element 17, can then be determined by detecting the real location of the tip 24 of the introduction element 17 within the initial broader tip image using image-based techniques like segmentation techniques that may be based on thresholding. The initial broader tip image 21 surely including the tip 24 of the introduction element 17 is schematically and exemplarily illustrated in FIG. 3. In FIG. 3 the dashed lines 20 indicate maximally possible bendings of the introduction element 17, which define the thickness of the initial tip image 21.

The imaging unit 6, 15 can be adapted to determine an axial tip slice and/or a sagittal tip slice and to generate an axial tip image and/or a sagittal tip image representing the axial tip slice and/or the sagittal tip slice, respectively, wherein the display 7 may be adapted to display the generated axial tip image and/or the sagittal tip image. In an embodiment the imaging unit 6, 15 is adapted to determine the tip slice such that it is perpendicular to the elongated body 25 of the introduction element 17.

The tracking unit 3, 4 is also adapted to determine the location of the elongated body 25 within the person 2, wherein the imaging unit 6, 15 may be adapted to determine a body slice within the person 2 including a length of the elongated body 25 and to generate a body image representing the body slice, wherein the display 7 is adapted to display the generated body image. In particular, the imaging unit 6, 15 may be adapted to determine the body slice such that the determined body slice includes a maximal portion of the length of the elongated body 25. The imaging unit 6, 15 may further be adapted to determine further body slices including further portions of the length of the elongated body 25 and to generate further body images representing the determined further body slices within the person 2, wherein the display 7 may be adapted to display the further body images. The imaging unit 6, 15 may be adapted to determine an axial tip slice and/or a sagittal body slice and to generate an axial tip image and/or a sagittal body image representing the axial tip slice and/or the sagittal body slice, respectively, wherein the display 7 may be adapted to display the generated axial tip image and/or the sagittal body image.

Thus, the display 7 can display one or several images showing, for instance, the tip 24 and/or the elongated body 25 of the introduction element 17 within the person 2 during the insertion process. For instance, an axial image plane may be chosen to include the tracked position of the tip 24 of the introduction element 17 and/or an image plane showing the maximum length of the introduction element 17 may be reconstructed from the ultrasound image volume and displayed on the display 7. Alternatively or in addition, a sagittal image may be adjusted to show the slice that contains the maximum portion or extent of the introduction element 17 and one or several further sagittal images corresponding to the reminder of the introduction element 17 may be presented, for instance, as thumbnail images, wherein the imaging unit may comprise an input unit 30 like a keyboard, a computer mouse, a touchpad, et cetera for allowing a user to select one of these thumbnail images to be displayed larger.

The imaging apparatus 24 further comprises a target location providing unit 26 for providing a target location, where the introduction element 17 is to be located within the person 2, wherein the imaging unit 6, 15 is adapted to determine a target slice within the person 2, which includes the target location, and to generate a target image representing the target slice. The display 7 is adapted to display the target image. Also the target image may be an axial target image or a sagittal target image. The target image may be shown together with one or several of the tip and body images. For instance, a target axial image, i.e. an image representing a target axial slice containing a desired location of the tip 24 of the introduction element 17, can be shown side-by-side with an axial tip image representing an axial tip slice containing the realtime location of the tip 24 of the introduction element 17. Or, for example, the axial target image can be displayed side-by-side with a sagittal body image representing a sagittal slice containing a longest portion of the length of the introduction element 17 or with a sagittal tip image representing a sagittal slice containing the tip 24 of the introduction element 17.

The target location providing unit 26 can be a storing unit, in which the target location is stored already and which is adapted to provide the stored target location. However, the target location providing unit 26 can also be a receiving unit for receiving the target location from another device via a wireless or wired data connection. The target location providing unit 26 can also be a user interface, in particular, a graphical user interface, which allows a user to indicate the target location on an image generated by the imaging unit 6, 15.

The imaging unit is preferentially adapted such that it covers a volume of the person 2, which allows the imaging unit to generate desired image slices, without having to physically displace the ultrasound probe 15. If in an embodiment the imaging unit does not cover an imaging volume being large enough for generating all desired image slices, the ultrasound probe 15 can be mounted on a moving unit controlled by the image generation unit, the location determination unit or another control unit depending on the locations of the desired slices within the person 2, which should be imaged. The moving unit can be, for instance, a motorized stepper that positions the ultrasound probe accordingly. This controlled moving unit can also be used, if instead of the three-dimensional ultrasound probe 15 a two-dimensional ultrasound probe having a one-dimensional array of ultrasound transducers is used, i.e. also in this case the ultrasound probe can be positioned such that a desired slice of the person 2 can be imaged. In order to control the moving unit accordingly, the tracked location of the introduction element within the person 2 is used.

If the imaging unit is adapted to cover an imaging volume, i.e. if the ultrasound probe comprises a two-dimensional array of ultrasound transducers, the imaging unit can be adapted to use the subset of ultrasound transducers from the transducer array, which can be used for generating an ultrasound image slice showing the introduction element, in particular, the tip of the introduction element. For this selection the imaging unit can use the tracked location of the introduction element within the person.

Figure 4:
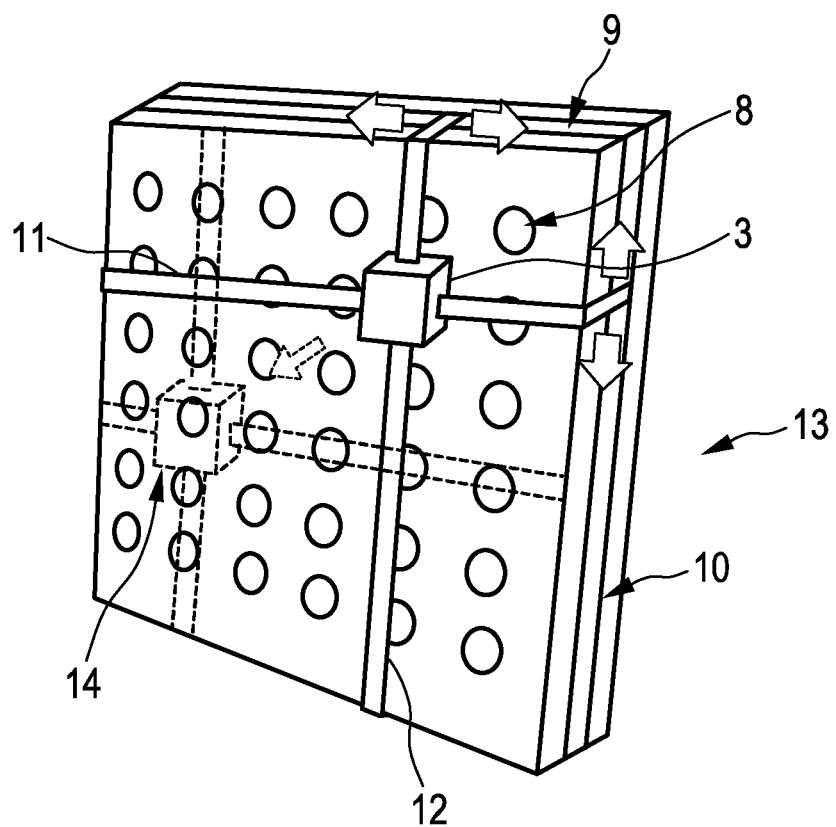

The imaging apparatus 24 may further comprise attaching elements 11, 12 for movably attaching the linear encoder 3 to the grid template 13 as schematically and exemplarily illustrated in FIG. 4. The small sides of the grid template 13 may comprise sliding elements 9, 10 which allow the attaching elements 11, 12 to be slid in vertical and horizontal directions, in order to move the linear encoder 3 to a desired opening 8 of the grid template 13, through which the introduction element 17 should be inserted into the person 2. After the linear encoder 3 has been moved to a desired opening 8, the linear encoder can be directly locked at this position or indirectly by locking the attaching elements 11, 12. For instance, the locking mechanism can use screws or other fixation means for directly fixing the linear encoder 3 or indirectly by fixing the attaching elements 11, 12. In FIG. 4 the actual position of the linear encoder is indicated by solid lines and a position, to which the linear encoder could be moved, is indicated by dashed lines 14.

Thus, the linear encoder 3 may be externally attached to a surface of the template grid 13, in particular, to the rear surface of the template grid 13, which is directed towards the person 2, by using movable attachment elements 11, 12, which allow for a smooth motion in a plane parallel to the grid template 13, in order to align the linear encoder 3 with a specific grid opening 8 through which the insertion of the introduction element should take place.

The attaching elements 11, 12 and the sliding elements 9, 10 may be adapted such that the ends of the attaching elements 11, 12 can be snapped on and off the sliding elements 9, 10. Thus, after the introduction element 17 has been inserted into the person 2 through the linear encoder 3, the linear encoder 3 with the attaching elements 11, 12 can be snapped off the grid template 13 and then be snapped on again, in order to position the linear encoder 3 at another opening 8 through which a further introduction element 17 may be inserted into the person 2. In this way the linear encoder 3 can be used for introducing several introduction elements 17 into the person 2 for performing, for instance, a HDR brachytherapy. If the brachytherapy system is used for performing an LDR brachytherapy, the attaching elements 11, 12 and the sliding elements 9, 10 may not be adapted to provide the snap on and off functionality, because during an LDR brachytherapy only one introduction element is inserted at a time. Moreover, in a further embodiment each grid opening can be fitted with a linear encoder at all times. The linear encoders may be activated one at a time, or they may be active at all times for simplicity.

Figure 5:
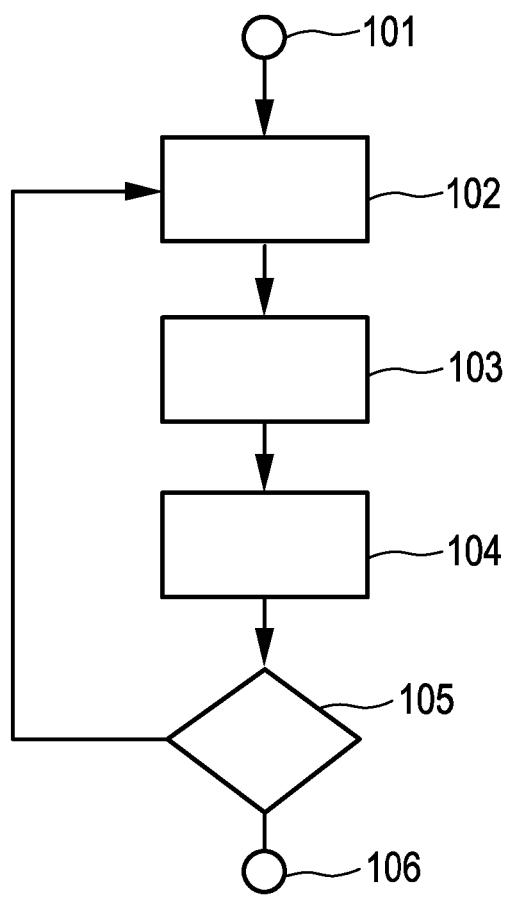
FIG. 5 shows a flowchart exemplarily illustrating an embodiment of an imaging method to be used with the brachytherapy system.

In the following an embodiment of an imaging method for imaging an introduction element within a living being will be described with reference to a flowchart shown in FIG. 5, wherein the introduction element is adapted to introduce a radiation source into the living being for performing a brachytherapy.

In step 101 the brachytherapy system 1 is initialized. In particular, the grid template 13 is arranged adjacent to the person 2 and the ultrasound probe 15 is transrectally introduced into the person 2. Moreover, the linear encoder 3 is placed at an opening 8 of the grid template 13, through which the introduction element 17 should be inserted into the person 2. In step 102 during the insertion of the introduction element 17 into the person 2 the tracking unit 3, 4 tracks the location of the introduction element 17 within the person 2 and in step 103 the imaging unit 6, 15 generates an image showing an inner part of the person 2, which includes the tracked position of the introduction element 17, based on the tracked location. In step 104 the generated image is shown on the display 7. In step 105 it is determined whether an abort criterion has been fulfilled. If this is the case, the imaging method ends in step 106. Otherwise the method continues with step 102. Thus, the tracking of the location of the introduction element, the generation of the image depending on the tracked location and the displaying of the image are performed in a loop, in order to provide a realtime image on the display 7, until an abort criterion is fulfilled. The abort criterion may be, for instance, whether a user has input via the input 30 that the method should be aborted, whether the tip of the introduction element has reached the target region, et cetera.

The above described imaging apparatus and imaging method can be used to assist in inserting an introduction element to be used for performing an LDR brachytherapy or a HDR brachytherapy. In case of an LDR brachytherapy the introduction element may be a needle, which is inserted to adhere to a pre-plan, wherein through the needle one or several radioactive radiation sources may be introduced into the person, in order to implant the one or several radioactive radiation sources in a target region for, for instance, one or several days. In case of HDR brachytherapy the radioactive radiation sources are preferentially not deposited in the target region, but are placed temporarily at different locations within the introduction element, for instance, for some minutes only, and then removed. If the imaging apparatus and imaging methods are used for performing a HDR brachytherapy, the knowledge about the entire three-dimensional shape and pose of the introduction element obtained during the insertion procedure can be used for determining the positions of the radioactive radiation sources, when they are introduced into the introduction element. Thus, the imaging apparatus and the imaging method can also be used to improve the accuracy of placing radioactive radiation sources during a HDR brachytherapy.

Although in above described embodiments the tracking unit uses a linear encoder for determining the location of the introduction element within the person, in other embodiments other tracking technologies can also be used. For instance, the tracking unit can be adapted to track the location of the introduction element by electromagnetic tracking and/or by optical shape sensing tracking.

Figure 6:
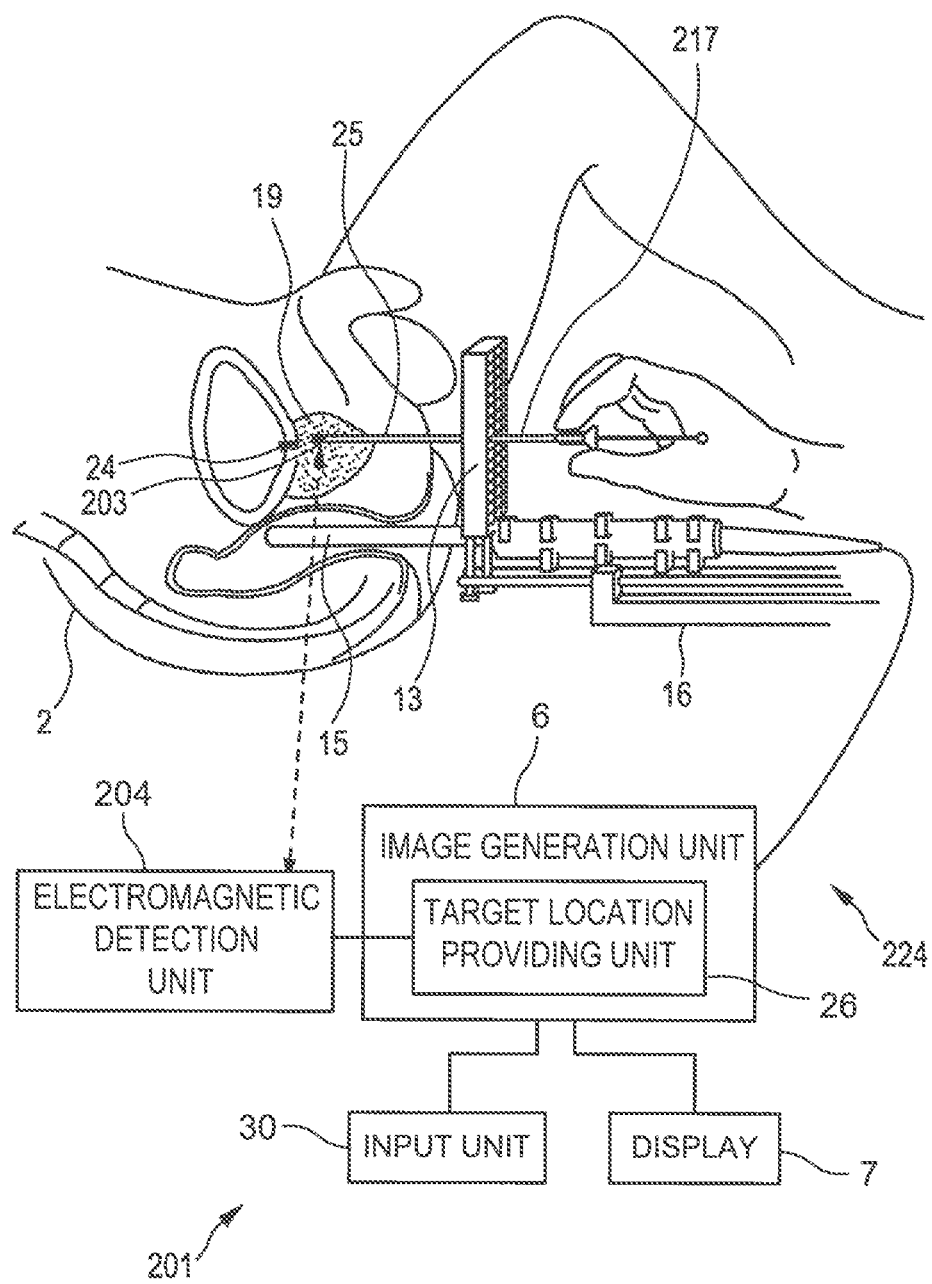
FIGS. 6 and 7 show further embodiments of the brachytherapy system.

FIG. 6 shows schematically and exemplarily a brachytherapy system 201 with an imaging apparatus 224, which is similar to the brachytherapy system 1 with the imaging apparatus 24 described above with reference to FIG. 1. However, in this embodiment the imaging apparatus 224 is adapted to determine the location of the introduction element 217 within the person 2 by electromagnetic tracking. For this reason the tip 24 of the introduction element 217 comprises an electromagnetic detection element 203 like a coil or another element, which is electromagnetically trackable, and an electromagnetic detection unit 204 for electromagnetically detecting the location of electromagnetic detection element 203 at the tip 24 of the introduction element 217 within the person 2. In this embodiment the electromagnetic detection element 203 and the electromagnetic detection unit 204 form the tracking unit. The electromagnetic detection unit 204 may be adapted to store the electromagnetically tracked locations of the tip 24 of the introduction element 217, which are tracked during the insertion process, in order to determine the location of the elongated body 25 of the introduction element 217 within the person 2. Thus, the path traversed by the introduction element can be saved, in order to have the shape and pose of the entire introduction element 217 within the person 2 available. By using electromagnetic tracking the position of the introduction element 217 within the person 2 can be accurately determined, even if the introduction element is deflected or bent.

Figure 7:
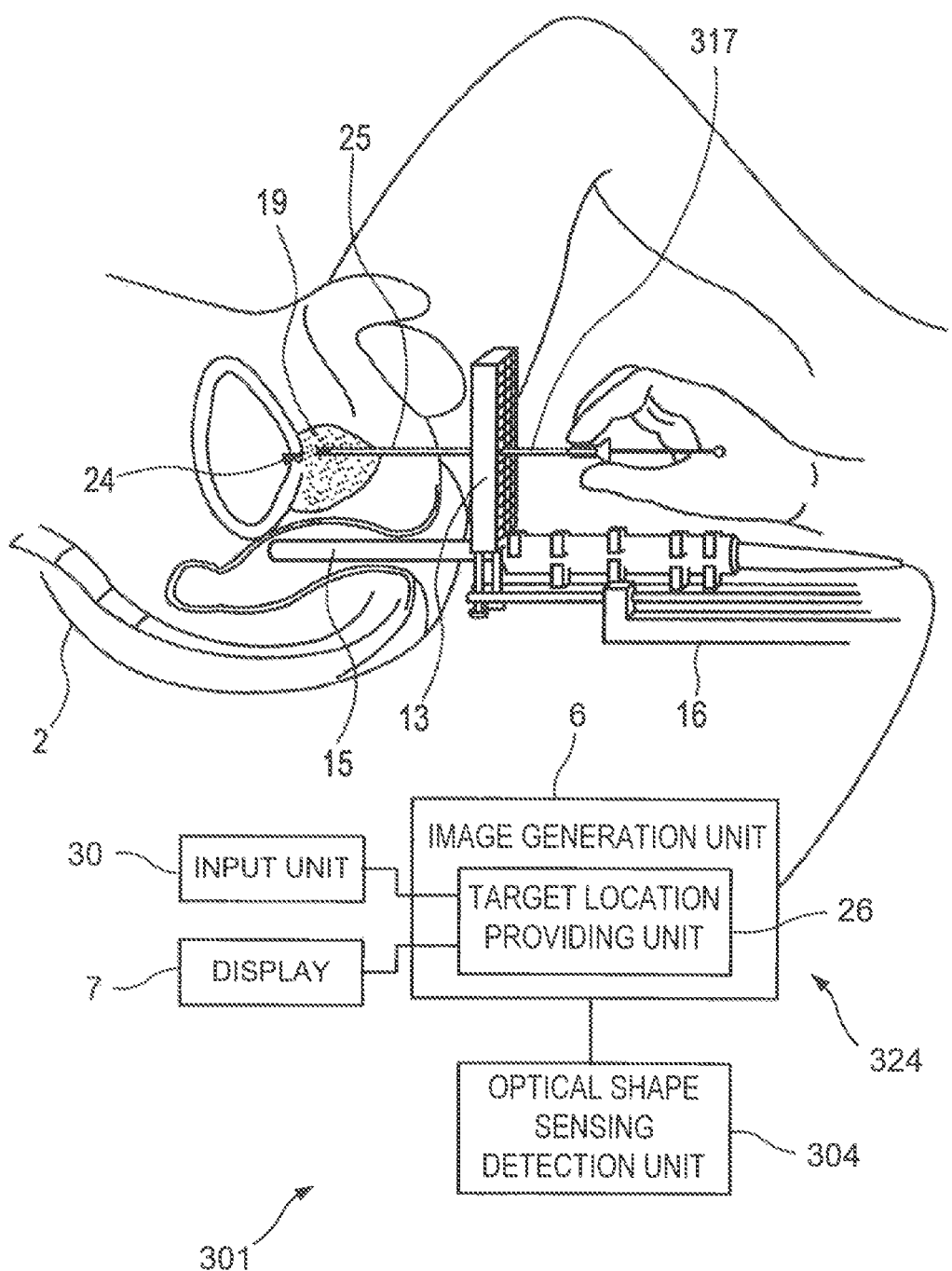

FIG. 7 shows schematically and exemplarily a further embodiment of a brachytherapy system 301 with an imaging apparatus 324, which uses optical shape sensing for tracking the location of the introduction element 317 within the person 2. Also in this embodiment the brachytherapy 301 with the imaging apparatus 324 is similar to the brachytherapy system 1 with the imaging apparatus 24 described above with reference to FIG. 1. However, in this embodiment the introduction element 317 is equipped with an optical shape sensing fiber, in particular, the entire length of the introduction element 317 comprises an optical shape sensing fiber, which is connected to an optical shape sensing detection unit 304 for determining the location of the entire length of the introduction element 317 including the location of the tip 24 of the introduction element 317 within the person 2 at all times. Also this allows accurately determining the location of the introduction element 317 within the person 2, even if the introduction element is deflected or bent.

Although in above described embodiments the introduction element is adapted to introduce a radiation source into the person for performing a brachytherapy, in other embodiments the introduction element can also be adapted to perform a biopsy. For instance, the introduction element can be a biopsy needle for performing a prostate biopsy procedure.

Although in FIGS. 1 to 3, 6 and 7 only a single introduction element is shown, also several introduction elements can be inserted into the person. Moreover, although in above described embodiments the living being is a person, in other embodiments the living being can also be an animal, and, although in above described embodiments the introduction element is introduced into the prostate, the introduction element may also be inserted into another part of the living being, especially into another organ.

Although in the embodiments described above with reference to FIGS. 1, 2 and 4 the linear encoder 3 is arranged at a rear surface of the grid template, i.e. on the surface directed towards the person, in other embodiments the linear encoder may be attached to the front surface of the grid template, i.e. to the surface directed away from the person.

Although in above described embodiments a linear encoder technique, an optical shape sensing tracking technique or an electromagnetic tracking technique is used for tracking the location of the introduction element within the living being, in other embodiments also other tracking techniques or a combination of these tracking techniques can be used. For instance, at least two of these tracking techniques can be used for determining the location of the introduction element within the living being at least twice, wherein these locations can be averaged for providing the tracked location, or a second tracking technique can be used as a kind of backup for a first tracking technique, in order to provide the location of the introduction element, even if the first tracking technique does not provide reliable locations or no locations at all. For instance, if the first tracking technique is the electromagnetic tracking technique and if it is disturbed, for example, due to an interference with a magnetic field, the second tracking technique, which may be the linear encoder technique or the optical shape sensing technique, can provide a reliable location of the introduction element within the living being.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of a location of an introduction element within a living being, the determination of slices within the living being including the location of the introduction element, the generation of images representing the slices, et cetera performed by one or several units or devices can be performed by any other number of units or devices. For instance, the location determination unit 4 can be integrated into the image generation unit 6 such that the image generation unit 6 may determine the location of the introduction element within the living being based on the position-encoded signal received from the linear encoder 3. Or, another device like an interventional workstation may receive the position-encoded signal and use the position-encoded signal for determining the location of the introduction element within the living being, which can be used by the image generation unit 6 for generating image slices depending on the determined location. The operations and/or the control of the imaging apparatus in accordance with the imaging method may be implemented as program code of a computer program and/or as dedicated hardware. The computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an imaging apparatus for imaging an introduction element like a needle or a catheter for performing a brachytherapy or a biopsy. A tracking unit tracks the location of the introduction element within a living being, an imaging unit like an ultrasound imaging unit generates an image showing an inner part of the living being, which includes the tracked location of the introduction element, based on the tracked location, and a display displays the image. During the brachytherapy or biopsy the display can always show the introduction element, without requiring a manual control. For instance, it is not necessary that a physician manually controls the position and image plane of the imaging unit. This allows for an accurate and fast insertion of the introduction element into the living being such that a target region is reliably reached.

The invention claimed is:

1. An imaging apparatus for imaging an introduction element within a living being, the introduction element being an elongated element having a tip and an elongated body comprising a scale on an outer surface of the elongated body, the introduction element adapted to be inserted into the living being through an opening within a holding element for holding the introduction element for performing a biopsy or for introducing a radiation source into the living being for performing a brachytherapy, wherein the imaging apparatus comprises:
   a tracking unit comprising a linear encoder adapted to read the scale on the outer surface of the elongated body of the introduction element to determine a linear location of the tip of the introduction element relative to the opening based on the scale, wherein the tracking unit is adapted to:
      track the location of the introduction element within the living being by determining the location of the tip and of the elongated body of the introduction element within the living being based on the determined linear location and a known location of the opening;
   an imaging unit for generating an image showing an inner part of the living being, which includes the tracked location of the introduction element, based on the tracked location, and
   a display for displaying the image.

2. The imaging apparatus as defined in claim 1, wherein the tracking unit is adapted to track the location of the introduction element by electromagnetic tracking and/or optical shape sensing tracking.

3. The imaging apparatus as defined in claim 1, wherein the tracking unit is adapted to track the location of the tip of the introduction element, wherein the imaging unit is adapted to determine a tip slice within the living being including the tracked location of the tip of the introduction element and to generate a tip image representing the tip slice, wherein the display is adapted to display the generated tip image.

4. The imaging apparatus as defined in claim 3, wherein the imaging unit is adapted to detect the tip of the introduction element within the tip image representing the determined tip slice by image processing, to determine a further tip slice including the detected tip of the introduction element, wherein the thickness of the tip slice is larger than the thickness of the further tip slice, and to generate a further tip image representing the further tip slice, wherein the display is adapted to display the generated further tip image.

5. The imaging apparatus as defined in claim 1, wherein the tracking unit is adapted to determine the location of the elongated body within the living being, wherein the imaging unit is adapted to determine a body slice within the living being including a length of the elongated body and to generate a body image representing the body slice, wherein the display is adapted to display the generated body image.

6. The imaging apparatus as defined in claim 5, wherein the imaging unit is adapted to determine the body slice based on the length of the elongated body.

7. The imaging apparatus as defined in claim 6, wherein the imaging unit is adapted to determine further body slices including further portions of the length of the elongated body and to generate further body images representing the determined further body slices within the living being, wherein the display is adapted to display the further body images.

8. The imaging apparatus as defined in claim 1, wherein the tracking unit is adapted to track the locations of at least two different parts of the introduction element within the living being, wherein the imaging unit is adapted to generate at least two images showing at least two inner parts of the living being, which include the locations of the at least two different parts of the introduction element, based on the tracked locations and wherein the display is adapted to display the at least two images.

9. The imaging apparatus as defined in claim 1, wherein the imaging apparatus further comprises one of a storage unit or a receiving unit, wherein the storage unit stores a target location and the receiving unit receives the target location, where the introduction element is to be located within the living being, wherein the imaging unit is adapted to determine a target slice within the living being, which includes the target location, and to generate a target image representing the target slice, wherein the display is adapted to display the target image.

10. The imaging apparatus as defined in claim 1, wherein the imaging unit is an ultrasound imaging unit.

11. A system for performing a brachytherapy or a biopsy, the system comprising:
   an introduction element being an elongated element having a tip and an elongated body for being inserted into a living being for performing a biopsy or for introducing a radiation source into the living being for performing a brachytherapy,
   a holding element comprising an opening for holding the introduction element, wherein the introduction element is adapted to be inserted into the living being through the opening, an imaging apparatus for imaging the introduction element within the living being as defined in claim 1.

12. An imaging method for imaging an introduction element within a living being, the introduction element being an elongated element having a tip and an elongated body comprising a scale on an outer surface of the elongated body, the introduction element adapted to be inserted into the living being through an opening within a holding element for holding the introduction element for performing a biopsy or for introducing a radiation source into the living being for performing a brachytherapy, wherein the imaging method comprises:
  determining a linear location of the tip of the introduction element relative to the opening based on the scale by using a linear encoder of a tracking unit adapted to read the scale on the outer surface of the elongated body of the introduction element and determining the location of the tip and of the elongated body of the introduction element within the living being based on the determined linear location and a known location of the opening, in order to track the location of the introduction element within the living being,
  electromagnetically track and store locations of the tip of the introduction element during insertion to determine the location of the elongated body of the introduction element within the living being,
  generating an image showing an inner part of the living being, which includes the tracked location of the introduction element, based on the tracked location by using an imaging unit, and
  displaying the image by using a display.

13. A non-transitory computer readable storage device comprising instructions stored thereon that, when executed by at least one processor of an imaging apparatus configured for imaging an introduction element within a living being, the introduction element being an elongated element having a tip and an elongated body comprising a scale on an outer surface of the elongated body, the introduction element adapted to be inserted into the living being through an opening within a holding element for holding the introduction element for performing a biopsy or for introducing a radiation source into the living being for performing a brachytherapy, the instructions comprising:
  determining a linear location of the tip of the introduction element relative to the opening based on the scale by using a linear encoder of a tracking unit adapted to read the scale on the outer surface of the elongated body of the introduction element and determining the location of the tip and of the elongated body of the introduction element within the living being based on the determined linear location and a known location of the opening, in order to track the location of the introduction element within the living being,
  electromagnetically tracking and storing locations of the tip of the introduction element during insertion to determine the location of the elongated body of the introduction element within the living being,
  generating an image showing an inner part of the living being, which includes the tracked location of the introduction element based on the tracked location by using an imaging unit, and
  displaying the image by using a display.

14. The non-transitory computer readable storage device of claim 13, further including determining location of a tip slice within the living being by the imaging unit, including the tracked location of the tip of the introduction element and generating a tip image representing the tip slice, and displaying the the generated tip image on the display.

15. The non-transitory computer readable storage device of claim 14, further including adapting the imaging unit to detect the tip of the introduction element within the tip image representing the determined tip slice by image processing, to determine a further tip slice including the detected tip of the introduction element, wherein the thickness of the tip slice is larger than the thickness of the further tip slice, and to generate a further tip image representing the further tip slice, wherein the display is adapted to display the generated further tip image.

16. The non-transitory computer readable storage device of claim 13, further including adapting the tracking unit to determine the location of the elongated body within the living being, wherein the imaging unit is adapted to determine a body slice within the living being including a length of the elongated body and to generate a body image representing the body slice, wherein the display is adapted to display the generated body image.

17. The non-transitory computer readable storage device of claim 13, further including adapting the imaging unit to determine the body slice based on the length of the elongated body.

* * * * *